US00PP13254P2

(12) United States Plant Patent
Heims

(10) Patent No.: US PP13,254 P2
(45) Date of Patent: Nov. 19, 2002

(54) ***CORYDALIS FLEXUOSA* PLANT NAMED 'GOLDEN PANDA'**

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/848,893

(22) Filed: May 3, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct form of Corydalis plant characterized by its distinctive yellow variegated leaves.

1 Drawing Sheet

The present invention relates to a new and distinct cultivar of Corydalis, of the family Papaveraceae, which originated from a mutation in tissue culture from an unpatented *Corydalis flexuosa* 'Blue Panda'.

This plant is characterized by the unique variegation of its foliage, which is patterened and colored with shades of yellow.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Corydalis flexuosa* 'Golden Panda' in bloom in early summer.

DETAILED PLANT DESCRIPTION

Figure 1:
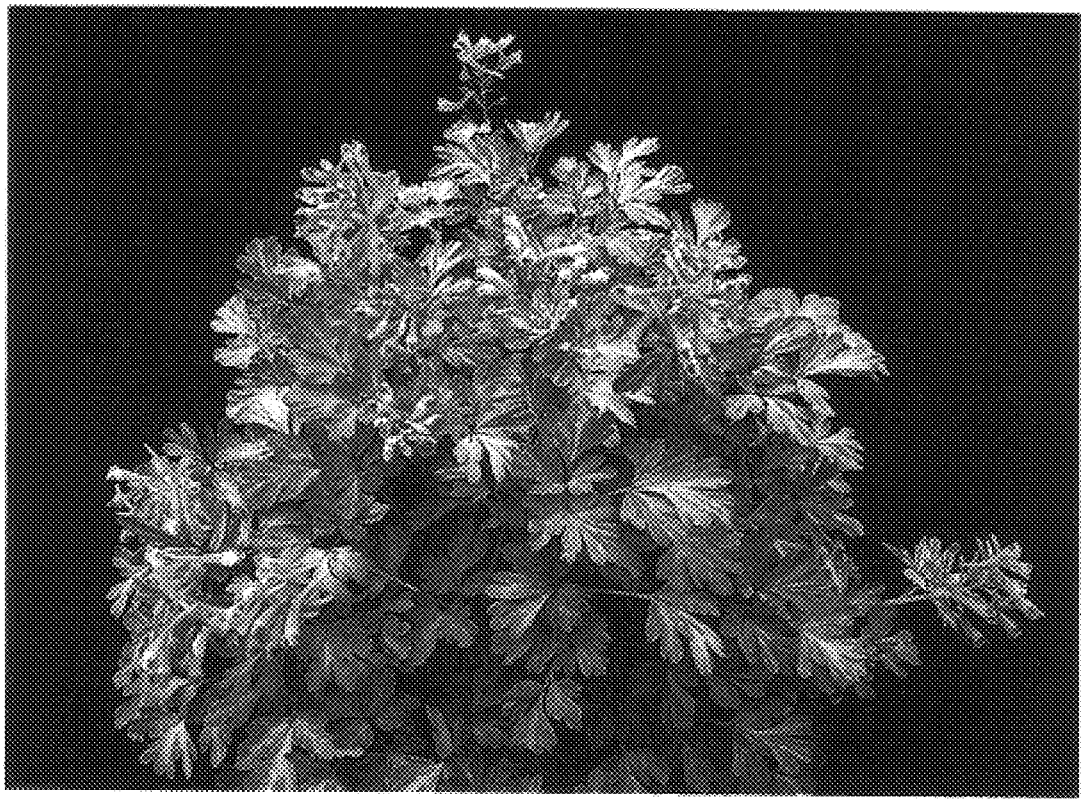

The following is a detailed description of the new *Corydalis flexuosa* variety based on observations of two-year-old specimens grown in two-gallon containers in a cool greenhouse in Canby, Oreg. The color descriptions are all based on The Royal Horticultural Society Colour Chart.

Botanical name: *Corydalis flexuosa.*
Cultivar name: 'Golden Panda'.
Plant:
- *Form.*—Clumping, herbaceous perennial, non-running habit.
- *Cold hardiness.*—USDA Zone 5.
- *Size.*—To 20 cm tall and 30 cm wide.

Stem:
- *Type.*—Rhizomatous, covered with fleshly scales.
- *Size.*—About 0.7 cm wide.
- *Color.*—Greyed Orange 174B.

Leaf:
- *Type.*—Compound, biternate.
- *Arrangement.*—Basal.
- *Shape.*—Ovate in outline.

- *Lobing/division.*—Each secondary leaflet is ternately divided and each division is 2–3 lobed.
- *Venation.*—Palmate.
- *Margins.*—Deeply divided, each lobe is entire.
- *Apex.*—Mucronulate.
- *Base.*—Lateral leaflets cordate, terminal leaflets truncate to cuneate.
- *Size.*—To 4 cm long and 3.25 cm wide.
- *Texture.*—Glabrous.
- *Petiole length.*—To 8 cm long.
- *Petiole texture.*—Glabrous.
- *Petiole color.*—Greyed Orange 174A–B to Greyed Red 182A.
- *Leaf color.*—Variegated with leaflet centers irregularly Yellow 4D to 2C streaking to greener toward margins Yellow Green 144A to Yellow Green 146C and 147C. Winter and early spring leaves are Green 138A with streaks of Yellow Green 145A. The base of each leaflet has a reddish spot like the petiole, Greyed Red 182A.

Inflorescence:
- *Type.*—Raceme.
- *Number of flowers.*—To about 11 per raceme.
- *Peduncle.*—Height — about 14 cm. Diameter — 0.15 cm. Color — Greyed Yellow 161A–B. Texture — Glabrous.
- *Pedicel.*—Length — to about 1.5 cm. Texture — Glabrous. Color — Greyed Red 179C–D.
- *Bracts.*—At pedicel base, leaf-like, lobed. Shape — Changes from reniform to orbicular to ovate to oblanceolate to linear going up the stem. Lobing decreases going up the stem from three leaflets and each leaflet 3–4 parted and lobed to one leaflet deeply lobed to a single lobe. Apex mucronulate. Size — Changes from bottom bract 1.7 cm wide and 1.4 cm deep to top bracts 5 mm long and 1.5 mm wide. Color — Green 138A heavily streaked Yellow 4D with lobe tips Greyed Red 182A.
- *Bloom period.*—April to June in Canby, Oreg.

Flower bud:
- *Size.*—About 1.7 cm long and 0.3 cm wide at the widest point prior to opening.
- *Description.*—Shaped like a young tadpole.
- *Color.*—Blue 106A–B with White 155D on bottom side. There is a purple spot on the upper petal lobe, Violet 87B.

Flower:

*Type.*—Zygomorphic.

*Shape.*—Tubular. Upper petal with a nectary spur which curves up. Nectary spur extends back from pedicel for 0.6 cm.

*Size.*—About 2.5 cm long and 0.6 cm at tip where it is widest.

*Color.*—Blue 106A–B on upper petal and tip of lower petal. White 155D on lower petal and inner petals. Upper and lower petal lobes have a purple spot, Violet 87B darkening to Violet-Blue 93B with maturity. Young Nectary Spurs have a purplish cast on the bottom, Violet 91B.

*Petal count.*—4.

*Sepal #.*—0.

*Stamen number.*—2.

*Anther number.*—6, three on each filament.

*Pistil.*—One, about 1.1 cm long and white 155A.

*Pollen.*—Yellow 13C.

*Filaments.*—Flat, translucent, 0.4 cm long.

*Fragrance.*—Reminiscent of sweet violet.

*Lastingness.*—A raceme blooms for about 3 weeks on the plant.

Fruit:

*Type.*—Narrowly linear, pendent capsules.

*Size.*—1.3 cm long and 1.5 mm wide.

*Color.*—Yellow Green 144B.

*Fertility.*—Low.

Seed:

*Shape.*—Flattened oval.

*Color.*—Black 202A.

Diseases: None observed on plants grown commercially in Canby, Oreg.

Pest resistance and susceptibility: Susceptible to aphids and spider mites like other Corydalis sp.

DESCRIPTION AND COMPARISON OF PARENT PLANT

*Corydalis flexuosa* 'Blue Panda' has pale blue-green, unmarked, fern-like leaves and sky-blue flowers with curved spurs. It is clump forming with a non-running habit. Compared to *Corydalis flexuosa* 'Blue Panda', *Corydalis flexuosa* 'Golden Panda' is a stable variegated form with leaves which turn golden in the summer. Both plants have excellent form, vigor, and blooms.

I claim:

1. A new and distinct form of Corydalis plant substantially as shown and described, characterized by a distinct yellow leaf coloration and pattern.

* * * * *